United States Patent
Holz et al.

(10) Patent No.: US 7,834,215 B2
(45) Date of Patent: Nov. 16, 2010

(54) UNSYMMETRICALLY SUBSTITUTED PHOSPHOLANE CATALYSTS

(75) Inventors: Jens Holz, Kessin (DE); Armin Boerner, Rostock (DE); Odalys Esperanza Zayas Vargas, Rostock (DE); Juan Jose Almena Perea, Hanau (DE); Axel Monsees, Frankfurt (DE); Renat Kadyrov, Frankfurt (DE); Thomas Riermeier, Ober-Ramstadt (DE)

(73) Assignee: Evonik Degussa GmbH, Essen (DE)

( * ) Notice: Subject to any disclaimer, the term of this patent is extended or adjusted under 35 U.S.C. 154(b) by 68 days.

(21) Appl. No.: 11/908,343

(22) PCT Filed: Mar. 2, 2006

(86) PCT No.: PCT/EP2006/060409

§ 371 (c)(1),
(2), (4) Date: Sep. 11, 2007

(87) PCT Pub. No.: WO2006/100169

PCT Pub. Date: Sep. 28, 2006

(65) Prior Publication Data

US 2008/0200695 A1    Aug. 21, 2008

(30) Foreign Application Priority Data

Mar. 23, 2005    (DE) .................... 10 2005 014 055

(51) Int. Cl.
C07F 9/6568 (2006.01)
C07F 9/572 (2006.01)
(52) U.S. Cl. ........................... 568/12; 548/412
(58) Field of Classification Search ................. 548/412; 568/12
See application file for complete search history.

(56) References Cited

U.S. PATENT DOCUMENTS

| | | | |
|---|---|---|---|
| 5,093,534 A | 3/1992 | Ludwig et al. | |
| 6,331,657 B1 | 12/2001 | Kaizik et al. | |
| 6,403,837 B1 | 6/2002 | Hess et al. | |
| 6,482,992 B2 | 11/2002 | Scholz et al. | |
| 6,492,544 B2 | 12/2002 | Krimmer et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Rottger et al. | |
| 6,573,389 B1 | 6/2003 | Bosch et al. | |
| 6,818,770 B2 | 11/2004 | Selent et al. | |
| 6,924,389 B2 | 8/2005 | Jackstell et al. | |
| 6,956,133 B2 | 10/2005 | Jackstell et al. | |
| 7,009,068 B2 | 3/2006 | Schmutzler et al. | |
| 7,109,346 B2 | 9/2006 | Beller et al. | |
| 7,138,552 B2 | 11/2006 | Kaizik et al. | |
| 7,161,020 B2 | 1/2007 | Selent et al. | |
| 7,193,116 B2 | 3/2007 | Moeller et al. | |
| 7,217,828 B2 | 5/2007 | Selent et al. | |
| 7,317,130 B2 | 1/2008 | Moeller et al. | |
| 7,345,185 B2 | 3/2008 | Ortmann et al. | |
| 2003/0144559 A1 | 7/2003 | Hess et al. | |
| 2003/0195368 A1 | 10/2003 | Rottger et al. | |
| 2004/0260091 A1* | 12/2004 | Berens ........................ 544/243 |
| 2005/0171371 A1 | 8/2005 | Borner et al. | |
| 2005/0209455 A1 | 9/2005 | Boerner et al. | |
| 2006/0052624 A1* | 3/2006 | Galland et al. ............... 558/338 |
| 2006/0089469 A1 | 4/2006 | Komarov et al. | |
| 2006/0241324 A1 | 10/2006 | Moeller et al. | |
| 2007/0112219 A1 | 5/2007 | Ortmann et al. | |
| 2007/0117995 A1 | 5/2007 | Ortmann et al. | |
| 2007/0123733 A1 | 5/2007 | Boerner et al. | |
| 2007/0149781 A1 | 6/2007 | Riermeier et al. | |
| 2007/0179301 A1 | 8/2007 | Boerner et al. | |
| 2007/0197799 A1 | 8/2007 | Holz et al. | |
| 2007/0282130 A1 | 12/2007 | Borgmann et al. | |

FOREIGN PATENT DOCUMENTS

| | | |
|---|---|---|
| EP | 1 318 155 | 6/2003 |
| EP | 1 318 155 A1 * | 6/2003 |

OTHER PUBLICATIONS

Basra et al. "Efficient asymmetric hydrogenation with rhodium complexes of C1-symmetric 2,5-dimethylphospholane-diphenylphosphines" Dalton Transactions, 2004, pp. 1901-1905.*

Basra, et al., "Efficient asymmetric hydrogenation with rhodium complexes of $C_1$asymmetric 2,5-dimethylphospholane-diphenylphosphines", Dalton Transactions, vol. 12, pp. 1901-1905, 2004.

(Continued)

*Primary Examiner*—Joseph R Kosack
(74) *Attorney, Agent, or Firm*—Oblon, Spivak, McClelland, Maier & Neustadt, L.L.P.

(57) ABSTRACT

The present invention is based on new ligand systems of the general formula (I). These ligand systems can be used advantageously in transition metal-catalyzed asymmetric syntheses. Likewise encompassed are the transition metal complexes thus prepared, a process for preparing the ligands and the use of the complexes in asymmetric synthesis.

(I)

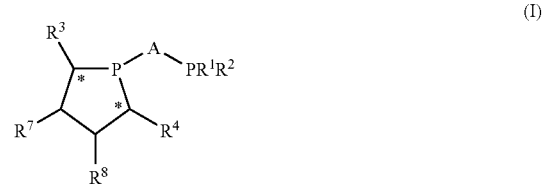

13 Claims, 1 Drawing Sheet

OTHER PUBLICATIONS

U.S. Appl. No. 12/373,921, filed Jan. 15, 2009, Hess, et al.
U.S. Appl. No. 12/515,967, filed May 22, 2009, Selent, et al.
U.S. Appl. No. 12/594,602, filed Oct. 5, 2009, Selent, et al.
Hydroformylation, Wikipedia, the free encyclopedia, http://en.wikipedia.org/wiki/Hydroformylation, 2010.

Renat Kadyrov, et al. "Efficient Enantioselective Synthesis of Optically Active Diols by Asymmetric Hydrogenation with Modular Chiral Metal Catalysts" Wiley InterScience, Communication, Asymmetric Synthesis, Angew. Chem. Int. Ed. 2009, vol. 48 (pp. 7556-7559), www.angewandte.org.

* cited by examiner

UNSYMMETRICALLY SUBSTITUTED PHOSPHOLANE CATALYSTS

The present invention is directed to new bisphosphane ligands and catalysts of the phospholane type. In particular, the invention relates to ligands of the general formula (I).

Enantiomerically enriched chiral ligands are used in asymmetric synthesis and asymmetric catalysis. It is essential here that the electronic and the stereochemical properties of the ligands are adjusted optimally to the particular catalysis problem. An important aspect of the success of these classes of compounds is attributed to the creation of a particularly asymmetric environment of the metal centre by these ligand systems. In order to utilize such an environment for an effective transfer of chirality, it is advantageous to control the flexibility of the ligand system as an inherent limitation of the asymmetric induction.

Within the substance class of the phosphorus-containing ligands, cyclic phosphines, especially the phospholanes, have achieved particular significance. Bidentate, chiral phospholanes are, for example, the DuPhos and BPE ligands used in asymmetric catalysis (Cobley, Christopher J.; Johnson, Nicholas B.; Lennon, Ian C.; McCague, Raymond; Ramsden, James A.; Zanotti-Gerosa, Antonio. The application of DuPHOS rhodium(I) catalysts for commercial scale asymmetric hydrogenation. Asymmetric Catalysis on Industrial Scale (2004), 269-282).

In the ideal case, however, a variously modifiable, chiral ligand basic skeleton is available, which can be varied within a wide range in relation to its steric and electronic properties.

WO03/084971 presents ligand and catalyst systems with which extremely positive results can be achieved especially in hydrogenation. In particular, the catalyst types deriving from maleic anhydride and the cyclic maleimide apparently create, in their property as chiral ligands, such a good environment around the central atom of the complex used that these complexes are superior to the best hydrogenation catalysts known to date for some hydrogenations.

Unsymmetrically substituted bisphospholane ligands and catalysts are presented, for example, by Pringle et al. and in the European Patent Applications EP1124833, EP1243591, EP1318155 and EP1318156. These derive substantially from the known DuPhos ligands (Dalton Transactions 2004, 12, 1901-5) or have flexible —($CH_2$)— units as a bridge.

However, it is also known that a catalyst is not applicable equally efficiently to all catalysis problems. Instead, the situation is such that certain catalysts can be used efficiently for selected catalysis processes and are less suitable for other purposes. It is therefore still important to have a high diversity of catalyst structures ready to be able to handle a maximum number of catalysis problems optimally.

It is therefore an object of the present invention to specify further ligand structures which can be used successfully in enantioselective catalysis. The ligands should be preparable in a simple manner from readily available precursor compounds, be stable in industrial application and, from economical and ecological points of view, be superior to the known prior art catalysts.

This object is achieved in accordance with the claims. Claims 1 and 2 relate to the ligand systems. Claims 3 and 4 are directed to inventive complexes. Claim 5 relates to a preferred embodiment for the preparation of the inventive ligands and claims 6 to 13 encompass the use of the catalysts described in asymmetric synthesis.

By providing ligand systems having the structure of the general formula (I)

in which
* represents a stereocentre,
$R^3$ and $R^4$ are each independently selected from the group consisting of
($C_1$-$C_8$)-alkyl, ($C_1$-$C_8$)-alkoxy, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl,
$R^7$ and $R^8$ are each independently H, $R^3$, or
$R^3$ and $R^7$ and/or $R^7$ and $R^8$ and/or $R^8$ and $R^4$ are joined to one another via a ($C_3$-$C_5$)-alkylene bridge,
$R^1$ and $R^2$ are each independently ($C_1$-$C_8$)-alkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl, ($C_1$-$C_8$)-alkyl-O, ($C_6$-$C_{18}$)-aryl-O, ($C_7$-$C_{19}$)-aralkyl-O, ($C_3$-$C_8$)-cycloalkyl-O, ($C_1$-$C_8$)-alkyl-NH, ($C_6$-$C_{18}$)-aryl-NH, ($C_7$-$C_{19}$)-aralkyl-NH, ($C_3$-$C_8$)-cycloalkyl-NH, (($C_1$-$C_8$)-alkyl)$_2$N, (($C_6$-$C_{18}$)-aryl)$_2$N, (($C_7$-$C_{19}$)-aralkyl)$_2$N, (($C_3$-$C_8$)-cycloalkyl)$_2$N,
A is a $C_2$ bridge where both carbon atoms have $sp^2$ hybridization and form part of a 3-, 4-, 5-, 6-, 7- or 8-membered ring system optionally having heteroatoms and where this ring system is substituted by at least one electron-withdrawing group selected from the group consisting of fluorine, chlorine, $CF_3CO$, $CF_3SO_2$, $CF_3$, $CnF_{2n+1}$ when A is a 1,2-bridged phenyl ring, the solution to the stated object is achieved in an extremely simple but no less advantageous manner. The ligand systems described can be used in a simple way in asymmetric synthesis and afford good to very good results, for example, in the asymmetric hydrogenation of various organic derivatives, for example β-acetamidocinnamic esters.

It is advantageous when the part-system A of the inventive ligand system is substituted on one side by the following phospholane substructures, where n in this case may assume a value of 1, 2 or 3 and R may be ($C_1$-$C_8$)-alkyl:

In this ring system, n and m may each independently be 0 or 1, and $Y^1$, $Y^2$, $Y^3$ and $Y^4$ are each independently selected from the group consisting of NH, NR, O, S, $CH_2$, C=O, C=S, C=NH, C=NR, S=O, P=O and/or $Y^1$ and $Y^2$ or $Y^2$ and $Y^3$ or $Y^3$ and $Y^4$ may optionally be mono- or polyunsaturated $(C_3-C_5)$-alkylene bridges, where R" is $(C_1-C_8)$-alkyl, $(C_6-C_{18})$-aryl, $(C_7-C_{19})$-aralkyl, $(C_1-C_8)$-alkyl-$(C_6-C_{18})$-aryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, an electron-withdrawing group selected from the group consisting of fluorine, chlorine, $CF_3CO$, $CF_3SO_2$, $CF_3$, $CnF_{2n+1}$, and the broken line may mean possible further double bonds. In the case that the present ring system is a 1,2-bridged phenyl ring, reference is made to the restriction outlined at the outset. R is as defined below.

Also advantageous are those inventive ligand systems which, instead of A, have a ring system selected from the group consisting of For the bridging molecular moiety A, the person skilled in the art can in principle use any radical useful for the present purpose provided that it has a $C_2$ bridge where both carbon atoms have $sp^2$ hybridization and where the radical forms part of a 3-, 4-, 5-, 6-, 7- or 8-membered ring system. The above-addressed restriction with regard to the 1,2-bridging phenyl rings as the A radical therefore applies. The above-addressed ring systems may optionally have one or more heteroatoms. Useful heteroatoms are especially oxygen, sulphur or nitrogen atoms. Over and above the above-described $sp^2$ hybridization, they may have further unsaturation and may be of aromatic nature. They may be mono- or polysubstituted by further radicals, especially those selected from the group consisting of $(C_1-C_8)$-alkyl, $(C_1-C_8)$-alkoxy, HO—$(C_1-C_8)$-alkyl, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl.

The ring systems may additionally also have one or more substituents which exert a negative inductive effect on the ring system. The negative inductive effect leads to electron density being withdrawn from the ring system via σ-bonds and hence also the electron density of the partring system A being reduced. This has a crucial influence on the basicity of the phosphorus atoms bonded to this part-system A. Such substituents having a negative inductive effect are in particular formed from atoms or groups of atoms which, taken alone or together, have a greater electronegativity than the carbon atom and are thus electron-withdrawing groups. These are advantageously those selected from the group consisting of fluorine, chlorine, $CF_3CO$, $CF_3SO_2$, $CF_3$, $C_nF_{2n+1}$.

An advantageous part-ring system A is therefore one which is formed in accordance with a ring system of the following type:

in which

Q is O, NH, NH—NH, NR—NR, NOR, NR, S, $CH_2$ or $C=C(R)_2$,

R is H, $(C_1-C_8)$-alkyl, $(C_6-C_{18})$-aryl, $(C_7-C_{19})$-aralkyl, $(C_1-C_8)$-alkyl-$(C_6-C_{18})$-aryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, R' is R or R''' and R''' is one or more electron-withdrawing groups selected from the group consisting of fluorine, chlorine, $CF_3CO$, $CF_3SO_2$, $CF_3$, $CnF_{2n+1}$, where R' and R''' may each be present independently in the ring system once or more than once, up to eight times.

The carbon atoms shown in the general formula (I) and indicated with an * represent stereogenic centres which impart chirality to the molecule in question. However, it is also possible that, over and above the carbon atoms indicated with an *, further up to all carbon atoms in the phospholane ring form a stereogenic centre in the ligand system of the invention. Particularly suitable compounds are those of the general formula (I) which are present in maximum enantiomerically enriched form. These are especially suitable for transferring a chiral induction in the process underlying the catalysis to the substrate and are thus capable of generating a high enantiomeric enrichment in the product too. Particularly advantageous compounds are those of the general formula (I) which have an enantiomeric enrichment of >90%, more preferably 91%, 92%, 93%, 94% and most preferably ≧95%. Extremely preferably, the compound of the general formula (I) may also have an enantiomeric enrichment of >98%.

The invention also provides complexes which contain the inventive ligands of the formula (I) and at least one transition metal.

Suitable complexes, especially of the general formula (V), contain inventive ligands of the formula (V)

$$[M_xP_yL_zS_q]A_r \quad (V)$$

where, in the general formula (V), M is a transition metal centre, L are identical or different coordinating organic or inorganic ligands and P are inventive bidentate organophosphorus ligands of the formula (I), S represent coordinating solvent molecules and A represent equivalents of noncoordinating anions, where x and y are integers greater than or equal to 1, z, q and r are integers greater than or equal to 0.

There is an upper limit on the sum of y+z+q by virtue of the coordination centres available on the metal centres, but not all coordination sites need be occupied. Preference is given to complexes with octahedral, pseudooctahedral, tetrahedral, pseudotetrahedral, square planar coordination spheres which may also be distorted around the particular transition metal centre. The sum of y+z+q in such complexes is less than or equal to 6.

The inventive complexes contain at least one transition metal atom or ion, in particular of palladium, platinum, rhodium, ruthenium, osmium, iridium, cobalt, nickel or copper, in any catalytically relevant oxidation state.

Preference is given to complexes having fewer than four metal centres, particular preference to those having one or two metal centres. The metal centres may be occupied by various metal atoms and/or ions.

Preferred ligands L of such complexes are halide, particularly Cl, Br and I, diene, particularly cyclooctadiene, norbornadiene, olefin, particularly ethylene and cyclooctene, acetato, trifluoroacetato, acetylacetonato, allyl, methallyl, alkyl, particularly methyl and ethyl, nitrile, particularly acetonitrile and benzonitrile, and also carbonyl and hydrido ligands.

Preferred coordinating solvents S are ethers, amines, particularly triethylamine, alcohols, particularly methanol, ethanol, i-propanol, and aromatics, particularly benzene and cumene, DMF or acetone.

Preferred noncoordinating anions A are trifluoroacetate, trifluoromethanesulphonate, $BF_4$, $ClO_4$, $PF_6$, $SbF_6$ and $BAr_4$, where Ar may be ($C_6$-$C_{18}$)-aryl.

The individual complexes may contain different molecules, atoms or ions of the individual constituents M, P, L, S and A.

Among the ionic complexes, preference is given to compounds of the $[RhP(diene)]^+A^-$ type where P represents an inventive ligand of the formula (I).

The invention also provides a process for preparing the inventive ligands with differently substituted phosphorus atoms, in which a compound of the general formula (II) or (II')

in which
A may be as defined at the outset,
X is a nucleofugic leaving group and
$R^1$ and $R^2$ may each be as defined above is reacted with a compound of the general formula (III)

in which $R^3$, $R^4$, $R^7$ and $R^8$ may each be as defined above and M may be a metal from the group consisting of Li, Na, K, Mg, Ca, or is an organosilyl group, in such a way that an X group of (II) or (II') is substituted and the absent phosphine group $PR^1R^2$ is subsequently introduced into the product of the reaction of (III) with (II).

With regard to the preparation of the starting compounds and conditions in the reactions in question, reference is made to the following literature (DE10353831; WO03/084971; EP592552; U.S. Pat. No. 5,329,015).

One possible preparation variant of the ligands and complexes is detailed in the following scheme:

The preparation of the inventive metal-ligand complexes just shown by way of example can be effected in situ by reaction of a metal salt or of a corresponding precomplex with the ligands of the general formula (I). In addition, a metal-ligand complex can be obtained by reacting a metal salt or an appropriate precomplex with the ligands of the general formula (I) and subsequent isolation.

Examples of such metal salts are metal chlorides, bromides, iodides, cyanides, nitrates, acetates, acetylacetonates, hexafluoroacetylacetonates, tetrafluoroborates, perfluoro-acetates or triflates, especially of palladium, platinum, rhodium, ruthenium, osmium, iridium, cobalt, nickel or copper.

Examples of the precomplexes are:
cyclooctadienepalladium chloride, cyclooctadienepalladium iodide,
1,5-hexadienepalladium chloride, 1,5-hexadienepalladium iodide, bis(dibenzylideneacetone)palladium, bis(acetonitrile)palladium(II) chloride, bis(acetonitrile)-palladium (II) bromide, bis(benzonitrile)palladium(II) chloride, bis (benzonitrile)palladium(II) bromide, bis-(benzonitrile) palladium(II) iodide, bis(allyl)palladium, bis(methallyl) palladium, allylpalladium chloride dimer, methallylpalladium chloride dimer, tetramethylethylenediaminepalladium dichloride, tetramethylethylenediamine-palladium dibromide, tetramethylethylenediaminepalladium diiodide, tetramethylethylenediaminepalladium dimethyl,
cyclooctadieneplatinum chloride, cyclooctadieneplatinum iodide, 1,5-hexadieneplatinum chloride,
1,5-hexadieneplatinum iodide, bis(cyclooctadiene)platinum, potassium ethylenetrichloroplatinate,
cyclooctadienerhodium(I) chloride dimer, norbornadiene-rhodium(I) chloride dimer,
1,5-hexadienerhodium(I) chloride dimer, tris(triphenylphosphine)rhodium(I) chloride, hydridocarbonyltris(triphenylphosphine)rhodium(I) chloride,
bis(norbornadiene)rhodium(I) perchlorate, bis(norbornadiene)rhodium(I) tetrafluoroborate, bis(norbornadiene)-rhodium(I) triflate,
bis(acetonitrilecyclooctadiene)rhodium(I) perchlorate, bis (acetonitrilecyclooctadiene)rhodium(I) tetrafluoro-borate, bis(acetonitrilecyclooctadiene)rhodium(I) triflate,
bis(acetonitrilecyclooctadiene)rhodium(I) perchlorate, bis (acetonitrilecyclooctadiene)rhodium(I) tetrafluoro-borate, bis(acetonitrilecyclooctadiene)rhodium(I) triflate, 1,5-cyclooctadienerhodium(I) acetoacetonate salts with halide, triflate, tetrafluoroborate, perchlorate anions,
cyclopentadienerhodium(III) chloride dimer, pentamethylcyclopentadienerhodium(III) chloride dimer,
(cyclooctadiene)Ru($\eta^3$-allyl)$_2$, ((cyclooctadiene)Ru)$_2$-(acetate)$_4$, ((cyclooctadiene)Ru)$_2$(trifluoroacetate)$_4$, RuCl$_2$ (arene) dimer, (RuareneI$_2$)$_2$, tris (triphenylphosphine)-ruthenium(II) chloride, cyclooctadieneruthenium(II) chloride, OsCl$_2$ (arene) dimer, cyclooctadieneiridium(I) chloride dimer, bis(cyclooctene)iridium(I) chloride dimer,
bis(cyclooctadiene)nickel, (cyclododecatriene)nickel, tris (norbornene)nickel, nickel tetracarbonyl, nickel(II) acetylacetonate,
(arene)copper triflate, (arene)copper perchlorate, (arene)-copper trifluoroacetate, cobalt carbonyl.

The complexes based on one or more metals of the metallic elements and ligands of the general formula (I), especially from the group of Ru, Os, Co, Rh, Ir, Ni, Pd, Pt, Cu, may already be catalysts or be used to prepare inventive catalysts based on one or more metals of the metallic elements, especially from the group of Ru, Os, Co, Rh, Ir, Ni, Pd, Pt, Cu.

All inventive complexes are particularly suitable as a catalyst for asymmetric reactions. Particular preference is given to their use for asymmetric hydrogenation, hydro-formylation, rearrangement, allylic alkylation, cyclo-propanation, hydrosilylation, hydride transfer reactions, hydroborations, hydrocyanations, hydrocarboxylations, aldol reactions or Heck reaction.

Very particular preference is given to their use in the asymmetric hydrogenation of, for example, C=C, C=O or C=N bonds, in which they have high activities and selectivities, and hydroformylation. In particular, it is found to be advantageous here that the ligands of the general formula (I) can be adjusted very efficiently to the particular substrate and the catalytic reaction in steric and electronic terms by virtue of their simple, wide modifiability.

Particular preference is given to the use of the inventive complexes or catalysts for hydrogenating E/Z mixtures of prochiral N-acylated β-aminoacrylic acids or derivatives thereof. The N-acyl group used here may preferably be acetyl, formyl or urethane or carbamoyl protecting groups. Since both E and Z derivatives of these hydrogenation substrates can be hydrogenated in similarly good enantiomeric excesses, it is possible to hydrogenate an E/Z mixture of prochiral N-acylated β-aminoacrylic acids or derivatives thereof with excellent enantiomeric enrichments overall without preceding separation. With regard to the reaction conditions to be employed, reference is made to EP1225166. The catalysts mentioned here can be used in an equivalent manner.

In general, the β-amino acid precursors (acids or esters) are prepared by literature methods. In the syntheses of the compounds, it is possible to follow the general methods of Zhang et al. (G. Zhu, Z. Chen, X. Zhang *J. Org. Chem.* 1999, 64, 6907-6910) and Noyori et al. (W. D. Lubell, M. Kitamura, R. Noyori *Tetrahedron: Asymmetry* 1991, 2, 543-554) and Melillo et al. (D. G. Melillo, R. D. Larsen, D. J. Mathre, W. F. Shukis, A. W.Wood, J. R. Colleluori *J. Org. Chem.* 1987 52, 5143-5150). Starting from the corresponding 3-keto carboxylic esters, reaction with ammonium acetate and subsequent acylation affords the desired prochiral enamides.

The hydrogenation products can be converted to the β-amino acids by measures known to those skilled in the art (analogously to the a-amino acids).

In principle, the ligands and complexes/catalysts are used in a manner known to those skilled in the art in the form of a transfer hydrogenation ("Asymmetric transferhydrogenation of C=O and C=N bonds", M. Wills et al. Tetrahedron: Asymmetry 1999, 10, 2045; "Asymmetric transferhydrogenation catalyzed by chiral ruthenium complexes" R. Noyori et al. Acc. Chem. Res. 1997, 30, 97; "Asymmetric catalysis in organic synthesis", R. Noyori, John Wiley & Sons, New York, 1994, p. 123; "Transition metals for organic Synthesis" Ed. M. Beller, C. Bolm, Wiley-VCH, Weinheim, 1998, Vol. 2, p. 97; "Comprehensive Asymmetric Catalysis" Ed.: Jacobsen, E. N.; Pfaltz, A.; Yamamoto, H., Springer-Verlag, 1999), but it can also take place in the classical manner with elemental hydrogen. The process can accordingly work either by means of hydrogenation with hydrogen gas or by means of transfer hydrogenation.

In the enantioselective hydrogenation, the procedure is preferably to dissolve substrates to be hydrogenated and complex/catalyst in a solvent. As indicated above, the catalyst is preferably formed from a precatalyst in the presence of the chiral ligand by reaction or by prehydrogenation before the substrate is added.

Subsequently, hydrogenation is effected at hydrogen pressure of 0.1 to 100 bar, preferably 0.5 to 10 bar. The temperature in the hydrogenation should be selected such that the reaction proceeds sufficiently rapidly at the desired enantiomeric excesses but side reactions are prevented as far as possible. Advantageously, operation is effected at temperatures of −20° C. to 100° C., preferably 0° C. to 50° C.

The ratio of substrate to catalyst is determined by economic considerations. The reaction should proceed sufficiently rapidly with minimum complex/catalyst concentration. However, preference is given to working at a substrate/catalyst ratio between 50 000:1 and 10:1, preferably 1000:1 and 50:1. Further substrates hydrogenatable efficiently in accordance with the invention are a-enamides, itaconates, unprotected β-enamines.

Figure 1:
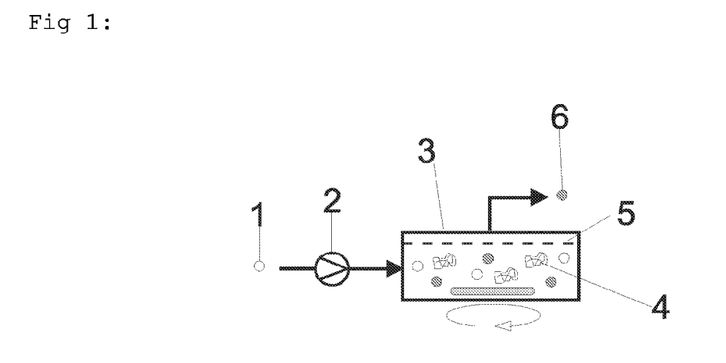
Figure 2:
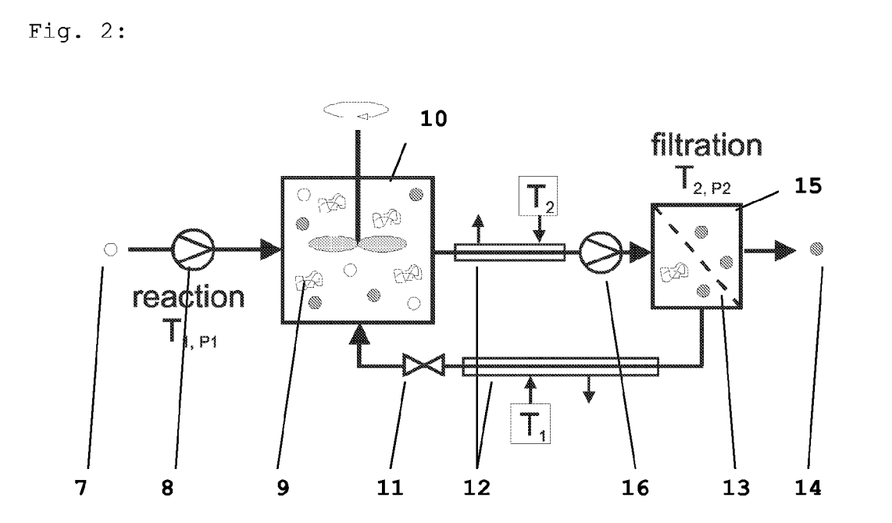

It is advantageous to use the ligands or complexes which have been polymer-enlarged in accordance with WO0384971 in catalytic processes which are carried out in a membrane reactor. In this case, the continuous mode, which is possible in this apparatus in addition to the batchwise and semicontinuous mode, can be carried out as desired in the crossflow filtration mode (FIG. 2) or as a dead-end filtration (FIG. 1).

Both process variants have been described in principle in the prior art (Engineering Processes for Bioseparations, Ed.: L. R. Weatherley, Heinemann, 1994, 135-165; Wandrey et al., Tetrahedron Asymmetry 1999, 10, 923-928).

In order that a complex/catalyst appears to be suitable for use in a membrane reactor, it has to satisfy a wide variety of criteria. First, it has to be ensured that an appropriately high retention capacity for the polymer-enlarged complex/catalyst has to be present so that there is satisfactory activity in the reactor over a desired period without complex/catalyst having to be replenished continually, which is disadvantageous in terms of economic operation (DE19910691). Moreover, the catalyst used should have an appropriate TOF (turnover frequency) in order to be able to convert the substrate to the products within economically viable periods.

In the context of the invention, polymer-enlarged complex/-catalyst is understood to mean the fact that one or more active units (ligands) which cause chiral induction, in a form suitable for this purpose, are copolymerized with further monomers, or that these ligands are coupled onto an already present polymer by methods known to those skilled in the art. Forms of the units which are suitable for copolymerization are well known to those skilled in the art and can be selected freely by them. The procedure is preferably to derivatize the molecule in question with groups capable of copolymerization depending on the type of copolymerization, for example by coupling onto acrylate/-acrylamide molecules in the case of copolymerization with (meth)acrylates. In this context, reference is made in particular to EP 1120160 and the polymer enlargements detailed there.

At the time of the invention, it was by no means obvious that the ligand systems presented here permit the development of catalyst systems which can be used under substantially more drastic conditions compared to the known prior art systems and simultaneously allow the advantageous properties and capabilities of the prior art systems to be confirmed. In particular, the unsymmetrically substituted phospholane-phosphine systems are superior to the symmetrical systems known in the prior art in that they can be prepared in a less expensive manner since they only require one molecule of the expensive chiral phospholane unit. In spite of this, the inventive ligands and catalyst systems feature high chiral induction in the underlying catalysis. $(C_1-C_8)$-Alkyl radicals are considered to be methyl, ethyl, n-propyl, isopropyl, n-butyl, isobutyl, sec-butyl, tert-butyl, pentyl, hexyl, heptyl or octyl including all of their bonding isomers.

The $(C_1-C_8)$-alkoxy radical corresponds to the $(C_1-C_8)$-alkyl radical with the proviso that it is bonded to the molecule via an oxygen atom.

$(C_2-C_8)$-Alkoxyalkyl means radicals in which the alkyl chain is interrupted by at least one oxygen function, where two oxygen atoms may not be joined to one another. The number of carbon atoms specifies the total number of carbon atoms present in the radical.

A $(C_3-C_5)$-alkylene bridge is a carbon chain having three to five carbon atoms, this chain being bonded to the molecule in question via two different carbon atoms.

The radicals described in the preceding paragraphs may be mono- or polysubstituted by halogens and/or nitrogen-, oxygen-, phosphorus-, sulphur-, silicon-containing radicals. These are in particular alkyl radicals of the type mentioned above which have one or more of these heteroatoms in their chain or which are bonded to the molecule via one of these heteroatoms.

$(C_3-C_8)$-Cycloalkyl is understood to mean cyclopropyl, cyclobutyl, cyclopentyl, cyclohexyl or cycloheptyl radicals, etc. They may be substituted by one or more halogens and/or nitrogen-, oxygen-, phosphorus-, sulphur-, silicon-containing radicals and/or have nitrogen, oxygen, phosphorus, sulphur atoms in the ring, for example 1-, 2-, 3-, 4-piperidyl, 1-, 2-, 3-pyrrolidinyl, 2-, 3-tetrahydrofuryl, 2-, 3-, 4-morpholinyl.

A $(C_3-C_8)$-cycloalkyl-$(C_1-C_8)$-alkyl radical denotes a cyclo-alkyl radical as detailed above which is bonded to the molecule via an alkyl radical as specified above.

In the context of the invention, $(C_1-C_8)$-acyloxy means an alkyl radical as defined above which has max. 8 carbon atoms and is bonded to the molecule via a COO function.

In the context of the invention, $(C_1-C_8)$-acyl means an alkyl radical as defined above which has max. 8 carbon atoms and is bonded to the molecule via a CO function.

A $(C_6-C_{18})$-aryl radical is understood to mean an aromatic radical having 6 to 18 carbon atoms. In particular, this includes compounds such as phenyl, naphthyl, anthryl, phenanthryl, biphenyl radicals, or systems of the above-described type fused to the molecule in question, for example indenyl systems which may optionally be substituted by halogen, $(C_1-C_8)$-alkyl, $(C_1-C_8)$-alkoxy, $NH_2$, $NH(C_1-C_8)$-alkyl, $N((C_1-C_8)$-alkyl$)_2$, OH, $CF_3$, NH $(C_1-C_8)$-acyl, $N((C_1-C_8)$-acyl$)_2$, $(C_1-C_8)$-acyl, $(C_1-C_8)$-acyloxy.

A $(C_7-C_{19})$-aralkyl radical is a $(C_6-C_{18})$-aryl radical bonded to the molecule via a $(C_1-C_8)$-alkyl radical.

In the context of the invention, a $(C_3-C_{18})$-heteroaryl radical denotes a five-, six- or seven-membered aromatic ring system composed of 3 to 18 carbon atoms and having heteroatoms, for example nitrogen, oxygen or sulphur, in the ring. Such heteroaromatics are considered in particular to be radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. This radical may be substituted with the same radicals as the abovementioned aryl radical.

A $(C_4-C_{19})$-heteroaralkyl is understood to mean a heteroaromatic system corresponding to the $(C_7-C_{19})$-aralkyl radical.

Useful halogens (Hal) include fluorine, chlorine, bromine and iodine.

PEG means polyethylene glycol.

N-acyl groups are understood to mean protecting groups which are generally used customarily in amino acid chemistry for the protection of nitrogen atoms. Particular examples include: formyl, acetyl, Moc, Eoc, phthalyl, Boc, Alloc, Z, Fmoc, etc.

A nucleofugic leaving group is understood essentially to mean a halogen atom, especially chlorine or bromine, or so-called pseudohalides. Further leaving groups may be tosyl, triflate, nosylate, mesylate.

In the context of the invention, the term enantiomerically enriched or enantiomeric excess is understood to mean the proportion of one enantiomer in a mixture with its optical antipode in a range of >50% and <100%. The ee value is calculated as follows:

([enantiomer1]–[enantiomer2])/([enantiomer1]+ [enantiomer2])=ee value

In the context of the invention, the specification of the inventive complexes and ligands includes all possible diastereomers, and shall also include the two optical anti-podes of a particular diastereomer.

The literature references cited in this document are considered to be included in the disclosure.

In the context of the invention, membrane reactor is understood to mean any reaction vessel in which the molecular weight-enlarged catalyst is enclosed in a reactor, while low molecular weight substances are fed to the reactor or can leave it. The membrane can be integrated directly into the reaction chamber or be installed outside it in a separate filtration module in which the reaction solution flows continuously or intermittently through the filtration module and the retentate is recycled into the reactor. Suitable embodiments include those described in WO98/22415 and in Wandrey et al. in 1998 yearbook, Verfahrenstechnik und Chemieingenieurwesen, VDI p. 151 ff.; Wandrey et al. in Applied Homogeneous Catalysis with Organometallic Compounds, Vol. 2, VCH 1996, p. 832 ff.; Kragl et al., Angew. Chem. 1996, 6, 684 ff.

In the context of the invention, a polymer-enlarged ligand/complex is understood to mean one in which the molecular weight-enlarged polymer has been bonded covalently to the ligands.

In the $CnF_{2n+1}$ group, n is an integer from 2 to 5.

Organosilyl groups are R'R''R'''Si radicals in which R', R'' and R''' may each independently be a $(C_1-C_8)$-alkyl group or a $(C_6-C_{18})$-aryl group.

DESCRIPTION OF THE DRAWINGS

FIG. 1 shows a membrane reactor with dead-end filtration. The substrate 1 is transferred via a pump 2 into the reaction chamber 3 which has a membrane 5. In the stirrer-operated reactor chamber are disposed the catalyst 4, the product 6 and unconverted substrate 1 as well as the solvent. Mainly low molecular weight 6 is filtered off through the membrane 5.

FIG. 2 shows a membrane reactor with crossflow filtration. Here, the substrate 7 is transferred via the pump 8 into the stirred reactor chamber in which the solvent, catalyst 9 and product 14 are also disposed. The pump 16 is used to establish a solvent flow which flows through an optionally present heat exchanger 12 into the crossflow filtration cell 15. Here, the low molecular weight product 14 is removed by means of the membrane 13. High molecular weight catalyst 9 is subsequently passed back into the reactor 10 with the solvent flow, optionally via the valve 11 and optionally again through a heat exchanger 12.

EXAMPLES $C_8H_9Cl_2NO_2$
Mol. Wt.: 222.068

H-952
$C_{20}H_{35}NO_2P_2$
Mol. Wt.: 383.445

-continued

H-952 K
C28H47BF4NO2P2Rh⁻
Mol. Wt.: 681,34

One equivalent (571 mg) of iPr₂P-SiMe₃ is added slowly at −78° C. to a solution of 666 mg of N-butyldichloromaleimide in 5 ml. The yellow-orange solution is allowed to warm to RT and stirred for 1.5 h. Subsequently, another one equivalent of trimethylsilylphospholane is added under cold conditions and the mixture is left to stir at RT for a further 2 hours.

NMR sample:

Compound A: +17.5 ppm and −7.6 ppm (2×d) in a proportion of 6% (possibly (THF-d₈) monooxide form);

Compound B: −3.4 ppm and −4.1 ppm (2×s) to an extent of 14% (?)

Compound C: −3.3 ppm and −4.4 ppm (2×d) to an extent of 74%

The solvent was removed and the residue taken up with 2 ml of THF and added dropwise at −20° C. via cannula to a solution of one equivalent (1.2 g) of [Rh(cod)₂]BF₄. After the precipitation with ether, filtration and washing, the complex was dried under reduced pressure.

NMR (CDCl₃): Compound A: +73.6 ppm (dd, 15.3 Hz and 147 Hz) and +60.8 ppm (dd, 15.3 Hz and 150 Hz) to an extent of 11%;
Compound B: +71.6 ppm (dd, 16.5 Hz and 150 Hz) and +65.0 ppm (dd, 16.5 Hz and 150 Hz) to an extent of 79%.

General Hydrogenation Method 0.005 mmol of precatalyst and 0.5 mmol of prochiral substrate are initially charged in an appropriate hydrogenation vessel under an H₂ atmosphere and temperature-controlled at 25° C. After the addition of the appropriate solvent (7.5 ml of methanol, tetrahydrofuran or dichloromethane) and pressure equalization (to atmospheric pressure), the hydrogenation is started by starting the stirring and commencing with the automatic recording of gas consumption under isobaric conditions. After the absorption of gas has ended, the experiment is ended, and conversion and selectivity of the hydrogenation are determined by means of gas chromatography.

Hydrogenation at 25° C., 1 bar, 100:1

| Catalyst | H-952 | | |
|---|---|---|---|
| Substrate | Sol. | t in min. | % ee |
| Me, COOMe, Ac-NH (E-1, AMe) | MeOH | 11' | 56.6 R |
| | THF | 7' | 56.6 R |
| | CH₂Cl₂ | 25' | 58.8 R |
| | MeOH | 200' | 64.9 R |
| | THF | 12.5 h (95%) | 66.6 R |
| | CH₂Cl₂ | 30' | 69.0 R |

-continued

| Catalyst | H-952 | | |
|---|---|---|---|
| Substrate | Sol. | t in min. | % ee |
| Me, COOBn, Ac-NH (E-OBn) (H-828 E) | MeOH | 400' (64%) | 65.0 R |
| | THF | 200' (93%) | 45.6 R |
| | CH₂Cl₂ | 120' (85%) | 63.0 R |
| i-Pr, COOEt, Ac-NH (H-672 E) (H-828 E) | THF | 18 h | 75.4 S |
| | CH₂Cl₂ | 100' | 63.2 S |

The invention claimed is:

1. A ligand system having the structure of general formula (I)

wherein
* represents stereocenter;
R³ and R⁴ are each independently selected from the group consisting of (C₁-C₈)-alkyl, (C₁-C₈)-alkoxy, HO—(C₁-C₈)-alkyl, (C₂-C₈)-alkoxyalkyl, (C₆-C₁₈)-aryl, (C₇-C₁₉)-aralkyl, (C₃-C₁₈)-heteroaryl, (C₄-C₁₉)-heteroaralkyl, (C₁-C₈)-alkyl-(C₆-C₁₈)-aryl, (C₁-C₈)-alkyl-(C₃-C₁₈)-heteroaryl, (C₃-C₈)-cycloalkyl, (C₁-C₈)-alkyl-(C₃-C₈)-cycloalkyl, and (C₃-C₈)-cycloalkyl-(C₁-C₈)-alkyl;
R⁷ and R⁸ are each independently H, R³, or
R³ and R⁷ and/or R⁷ and R⁸ and/or R⁸ and R⁴ are joined to one another via a (C₃-C₅)-alkylene bridge;
R¹ and R² are each independently (C₁-C₈)-alkyl, (C₆-C₁₈)-aryl, (C₇-C₁₉)-aralkyl, (C₃-C₁₈)-heteroaryl, (C₄-C₁₉)-heteroaralkyl, (C₁-C₈)-alkyl-(C₆-C₁₈)-aryl, (C₁-C₈)-alkyl-(C₃-C₁₈)-heteroaryl, (C₃-C₈)-cycloalkyl, (C₁-C₈)-alkyl-(C₃-C₈)-cycloalkyl, (C₃-C₈)-cycloalkyl-(C₁-C₈)-alkyl, (C₁-C₈)-alkyl-O, (C₆-C₁₈)-aryl-O, (C₇-C₁₉)-aralkyl-O, (C₃-C₈)-cycloalkyl-O, (C₁-C₈)-alkyl-NH, (C₆-C₁₈)-aryl-NH, (C₇-C₁₉)-aralkyl-NH, (C₃-C₈)-cycloalkyl-NH, ((C₁-C₈)-alkyl)₂N, ((C₆-C₁₈)-aryl)₂N, ((C₇-C₁₉)-aralkyl)₂N, or ((C₃-C₈)-cycloalkyl)₂N; and
A is a ring system having the following structure:

wherein

Q is O, NH, NH—NH, NR—NR, NOR, NR, S, CH$_2$ or C=C(R)$_2$;

R is H, (C$_1$-C$_8$)-alkyl, (C$_6$-C$_{18}$)-aryl, (C$_7$-C$_{19}$)-aralkyl, (C$_1$-C$_8$)-alkyl-(C$_6$-C$_{18}$)-aryl, (C$_3$-C$_8$)-cycloalkyl, (C$_1$-C$_8$)-alkyl-(C$_3$-C$_8$)-cycloalkyl, or (C$_3$-C$_8$)-cycloalkyl-(C$_1$-C$_8$)-alkyl;

R' is R or R'''; and

R''' is one or more electron-withdrawing groups selected from the group consisting of flourine, chlorine, CF$_3$CO, CF$_3$SO$_2$, CF$_3$, and CnF$_{2n+1}$.

2. The ligand system according to claim 1, wherein the formula (I) compound has an enantiomeric enrichment of >90%.

3. A complex, comprising:

a ligand according to claim 1; and at least one transition metal.

4. The complex according to claim 3 wherein the at least one transition metal is rhodium or ruthenium.

5. A process for preparing the ligand according to claim 1, comprising:

reacting a compound of general formula (II) or (II')

(II)

(II')

with a compound of general formula (III)

(III)

thereby forming a P-A bond; and wherein the compound of general formula (II) is reacted, subsequently replacing a remaining —X with a phosphine group having the structure PR$^1$R$^2$;

wherein A is a ring system having the following structure:

wherein

Q is O, NH, NH—NH, NR—NR, NOR, NR, S, CH$_2$ or C=C(R)$_{21}$;

R is H, (C$_1$-C$_8$)-alkyl, (C$_6$-C$_{18}$)-aryl, (C$_7$-C$_{19}$)-aralkyl, (C$_1$-C$_8$)-alkyl-(C$_6$-C$_{18}$)-aryl, (C$_3$-C$_8$)-cycloalkyl, (C$_1$-C$_8$)-alkyl-(C$_3$-C$_8$)-cycloalkyl, or (C$_3$-C$_8$)-cycloalkyl-(C$_1$-C$_8$)-alkyl;

R'' is R or R'''; and

R''' is one or more electron-withdrawing groups selected from the group consisting of fluorine, chlorine, CF$_3$CO, CF$_3$SO$_2$, CF$_3$, and CnF$_{2n+1}$ X is a nucleophilic leaving group; and R$^1$ and R$^2$ are each independently (C$_1$-C$_8$)-alkyl, (C$_6$-C$_{18}$)-aryl, (C$_7$-C$_{19}$)-aralkyl, (C$_3$-C$_{18}$)-heteroaryl, (C$_4$-C$_{19}$)-heteroaralkyl, (C$_1$-C$_8$)-alkyl-(C$_6$-C$_{18}$)-aryl, (C$_1$-C$_8$)-alkyl-(C$_3$-C$_{18}$)-heteroaryl, (C$_3$-C$_8$)-cycloalkyl, (C$_1$-C$_8$)-alkyl-(C$_3$-C$_8$)-cycloalkyl, (C$_3$-C$_8$)-cycloalkyl-(C$_1$-C$_8$)-alkyl, (C$_1$-C$_8$)-alkyl-O, (C$_6$-C$_{18}$)-aryl-O, (C$_7$-C$_{19}$)-aralkyl-O, (C$_3$-C$_8$)-cycloalkyl-O, (C$_1$-C$_8$)-alkyl-NH, (C$_6$-C$_{18}$)-aryl-NH, (C$_7$-C$_{19}$)-aralkyl-NH, (C$_3$-C$_8$)-cycloalkyl-NH, ((C$_1$-C$_8$)-alkyl)$_2$N, ((C$_6$-C$_{18}$)-aryl)$_2$N, ((C$_7$-C$_{19}$)-aralkyl)$_2$N, ((C$_3$-C$_8$)-cycloalkyl)$_2$N, R$^3$, R$^4$, R$^3$ and R$^4$ are each independently selected from the group consisting of (C$_1$-C$_8$)-alkyl, (C$_1$-C$_8$)-alkoxy, HO—(C$_1$-C$_8$)-alkyl, (C$_2$-C$_8$)-alkoxyalkyl, (C$_6$-C$_{18}$)-aryl, (C$_7$-C$_{19}$)-aralkyl, (C$_3$-C$_{18}$)-heteroaryl, (C$_4$-C$_{19}$)-heteroaralkyl, (C$_1$-C$_8$)-alkyl-(C$_6$-C$_{18}$)-aryl, (C$_1$-C$_8$)-alkyl-(C$_3$-C$_{18}$)-heteroaryl, (C$_3$-C$_8$)-cycloalkyl, (C$_1$-C$_8$)-alkyl-(C$_3$-C$_8$)-cycloalkyl, (C$_3$-C$_8$)-cycloalkyl-(C$_1$-C$_8$)-alkyl, R$^7$ and R$^8$ are each independently H, R$^3$, or R$^3$ and R$^7$ and/or R$^7$ and R$^8$ and/or R$^8$ and R$^4$ are joined to one another via a (C$_3$-C$_5$)-alkylene bridge; and M is a metal selected from the group consisting of Li, Na, K, Mg, and Ca, or is an organosilyl group.

6. A process for an asymmetric hydrogenation or hydroformylation of a substrate, comprising:

catalyzing the asymmetric reaction with a catalyst comprising the complex according to claim 4.

7. A process for asymmetric hydrogenation or hydroformylation, comprising:

catalyzing the asymmetric reaction with a catalyst comprising the complex according to claim 4.

8. The process according to claim 7, wherein an E/Z mixture of prochiral N-acylated β-aminoacrylic acid or derivatives thereof is hydrogenated.

9. The process according to claim 6, wherein the asymmetric reaction is a hydrogenation, and comprises hydrogenation with hydrogen gas or transfer hydrogenation.

10. The process according to claim 9, wherein the asymmetric reaction comprises hydrogen gas, and a hydrogen pressure is from 0.1 to 100 bar.

11. The process according to claim 9, wherein a temperature of the asymmetric hydrogenation is from −20° C. to 100° C.

12. The process according to claim 6, wherein a substrate/catalyst ratio is from 50 000:1 to 10:1.

13. The process according to claim 6, wherein the asymmetric reaction catalysis is in a membrane reactor.

* * * * *